(12) United States Patent
Baumann et al.

(10) Patent No.: US 6,422,778 B2
(45) Date of Patent: Jul. 23, 2002

(54) SURGICAL PREP SOLUTION APPLICATOR SYSTEM AND METHODS

(75) Inventors: Nicholas R. Baumann, St. Paul; Matthew T. Scholz, Woodbury; Robert P. Zaspel, St. Paul; Kent E. Lageson, Savage; Claude E. Cybulski, Lake Elmo, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/759,992

(22) Filed: Jan. 12, 2001

Related U.S. Application Data

(63) Continuation-in-part of application No. 09/561,556, filed on Apr. 28, 2000, which is a continuation-in-part of application No. 09/541,348, filed on Apr. 3, 2000, now abandoned.

(51) Int. Cl.⁷ .............................................. B05C 11/00
(52) U.S. Cl. ...................... 401/266; 401/183; 401/265; 401/203; 401/207; 401/134
(58) Field of Search ................................. 401/266, 261, 401/183, 265, 203, 196, 207, 6, 132, 134

(56) References Cited

U.S. PATENT DOCUMENTS

| | | |
|---|---|---|
| 2,932,840 A | 4/1960 | Lathrop |
| 3,133,309 A | 5/1964 | Miles |
| 3,393,963 A | 7/1968 | Nadal |
| 3,466,131 A | 9/1969 | Arcudi |
| 3,774,609 A | 11/1973 | Schwartzman |
| 3,847,151 A | 11/1974 | D'Alessandro et al. |
| 3,891,331 A | 6/1975 | Avery |
| 3,929,135 A | 12/1975 | Thompson |
| 4,148,318 A | 4/1979 | Meyer |
| 4,183,684 A | 1/1980 | Avery, Jr. |
| 4,342,522 A | 8/1982 | Mackles |
| 4,415,288 A | 11/1983 | Gordon et al. |
| 4,498,796 A | 2/1985 | Gordon et al. |
| 4,507,111 A | 3/1985 | Gordon et al. |
| 4,528,268 A | 7/1985 | Andersen et al. |
| 4,611,941 A | 9/1986 | Karliner et al. |
| 4,822,194 A | 4/1989 | Simonette |
| 4,889,441 A | 12/1989 | Tice |
| 4,925,327 A | 5/1990 | Wirt |
| 4,957,385 A | 9/1990 | Weinstein |
| 5,122,158 A | 6/1992 | Kuroda et al. |
| 5,147,337 A | 9/1992 | Plone |
| 5,240,339 A | 8/1993 | DeForest et al. |
| 5,299,877 A | 4/1994 | Birden |
| 5,364,367 A | 11/1994 | Banks et al. |
| 5,538,353 A | 7/1996 | DeHavilland |
| 5,577,851 A | 11/1996 | Koptis |
| 5,597,255 A | 1/1997 | Yager et al. |
| 5,658,084 A | 8/1997 | Wirt |
| 5,690,958 A | 11/1997 | McGrath |

FOREIGN PATENT DOCUMENTS

| | | |
|---|---|---|
| DE | 1 940 235 | 2/1971 |
| EP | 0 953 324 | 11/1999 |
| EP | 0 955 159 | 11/1999 |
| FR | 2 722 695 A1 | 1/1996 |

OTHER PUBLICATIONS

3M Dura Prep™ Sheet, Mar., 1988.

*Primary Examiner*—David J. Walczak
(74) *Attorney, Agent, or Firm*—John A. Burtis

(57) ABSTRACT

Systems and methods for applying or dispensing surgical prep solution. The applicator system includes a spreader element and a container of surgical prep solution. The spreader element includes a body with an orifice covered by a pad. The orifice is in fluid communication with a passage through an elongated stem connected to the body. The container may be collapsible with only limited recovery. The spreader element may include a receptacle for receiving the container.

33 Claims, 7 Drawing Sheets

SURGICAL PREP SOLUTION APPLICATOR SYSTEM AND METHODS

RELATED APPLICATIONS

This application is a continuation-in-part of U.S. patent application Ser. No. 09/561,556 filed on Apr. 28, 2000 and titled SURGICAL PREP SOLUTION DISPENSER WITH ATTACHABLE CONTAINER, which is a continuation-in-part of U.S. patent application Ser. No. 09/541,348 filed on Apr. 3, 2000 now abandoned and titled SURGICAL PREP SOLUTION DISPENSER WITH ATTACHABLE CONTAINER, both of which are hereby incorporated herein by reference in their entirety.

TECHNICAL FIELD

This invention relates to liquid applicators having particular utility in the field of antiseptic skin surface preparation. More particularly, this invention relates to articles and methods useful in applying pre-operative surgical scrubs or paints to skin.

BACKGROUND

Antiseptic preparation of patient's skin for surgery conventionally includes a 3–10 minute scrubbing of the affected area with a soap solution followed by the application of a water-soluble antiseptic paint solution. These solutions are generally applied with saturated sponges attached to a blade or held with forceps. These sponges are often saturated by soaking them in open pans of solution. Sometimes, sponges with attached handles are provided in a plastic pouch containing enough liquid to saturate the sponges.

While inexpensive, these techniques are messy and offer little control over inadvertent dripping of the solution into areas where it is undesired. Because many of the available solutions contain active ingredients such as alcohol and iodine, good control over the application has long been desirable.

Devices have been developed in an attempt to prevent the dripping of solution associated with these early techniques, and to reduce the time required for application of the antiseptic solution. In particular, the DURAPREP products commercially available from 3M Company of St. Paul, Minn. have enjoyed commercial success by providing substantially drip-free, convenient application. U.S. Pat. No. 4,925,327 describes a liquid applicator that incorporates a rigid, porous metering insert to regulate the flow rate of liquid disposed between the applicator handle and a foam sponge covering a major orifice of the handle. The liquid to be dispensed is contained in a rupturable reservoir removably affixed at the other major orifice of the handle.

U.S. Pat. No. 5,658,084 further discloses a liquid applicator in which the liquid is contained in a frangible ampoule inside the body of the applicator. This ampoule is supported and protected by a deformable element that prevents unintentional breakage of the ampoule from impacts during storage and handling before use. The applicator is actuated by pushing at least a portion of the frangible ampoule through an aperture in the deformable element and into contact with a means for breaking the ampoule.

Such ampoules are made of glass, in spite of the fact that sealed glass ampoules are relatively expensive. Many clinicians prefer to apply the prep in full aseptic attire (including sterile surgical gloves) and, therefore, it is important that the applicator that will be touched by those gloves be provided in a sterile condition. And since, for example, iodine based solutions decompose with exposure to gamma irradiation, manufacturers turn to gas sterilization with ethylene oxide gas to sterilize the outer surface of the container. Iodine solutions can form toxic by products such as iodohydrin (2-iodoethanol) when exposed to ethylene oxide sterilization, so they must be protected from exposure to this sterilant. Glass is a good barrier to agents such as ethylene oxide, unlike many other commonly used medical packaging materials, and so has been the material of choice for containing the prep solutions in spite of its cost.

While these described products have provided considerable advances, they are complex to manufacture, placing them beyond the means of some health care consumers. The art could still benefit from an applicator that could provide convenient, substantially drip-free dispensing of surgical preps at a lower cost.

SUMMARY OF THE INVENTION

The present invention provides a systems and methods for applying or dispensing surgical prep solution. Among the potential advantages of the systems and methods of the invention are the ability to dispense surgical prep solution substantially drip-free.

The applicator system includes a spreader element and a container of surgical prep solution. The spreader element preferably includes a body with at least one orifice covered by a pad. The orifice is in fluid communication with a passage through an elongated stem connected to the body.

The passage connects to a spout on the container when the surgical prep solution is to be dispensed. It may be preferred to angle the stem relative to the pad and, further, to provide a stem that is long enough to ensure that, if the applicator is used by a clinician with sterile gloved hands, the gloves do not come close to contacting the patient's skin so as to contaminate the gloves and violate aseptic technique.

As used in connection with the present invention, "surgical prep solution" includes skin and/or mucosa antiseptic compositions that may be useful for preparing the skin for other medical procedures such as the introduction of catheters, inoculations, etc. In some instances, surgical prep solutions used in connection with the invention may be film-forming when, e.g., applied to human or animal skin.

Surgical prep solutions used in connection with the present invention may include one or more of a variety of human skin-compatible antimicrobial agents. Examples of some suitable antimicrobial agents include, but are not limited to, chlorhexidine, triclosan, octenidene, quaternary ammonium functional surfactants, etc. It may be preferred, but not required, that the surgical prep solution include iodine or chlorhexidine in its composition. It may further be preferred that the surgical prep solution include alcohol in its composition. One suitable surgical prep solution may be, e.g., DURAPREP surgical prep solution available from 3M, St. Paul, Minn.

When using low viscosity surgical prep solutions (which may also be of relatively low surface tension), it may be preferred to provide a flow restrictor between the container and the pad. The flow restrictor partially restricts the flow of surgical prep solution from the container to the spreader element to enhance uniform filling of the pad with solution and reduce or prevent dripping. The flow restrictor may take a variety of forms as described below.

The container may, for example, be provided in a tube resembling a toothpaste tube. The container holds the surgical prep solution and includes a spout adapted to attach to the stem. It may be preferred that the container is rigid enough to act as a handle for the applicator system in combination with the stem.

The container is collapsible and compression of the container causes the surgical prep solution to flow from the container to the pad when the container is attached to the spreader element. The collapsible container preferably does not recover significantly when depressed.

This property of being collapsible without significant recovery can assist with the avoidance of dripping. Many commercially available containers are resilient and recover substantially all of their original volume after compression. In many instances this results in refilling of the container with air. If a recovered container is used, the clinician could be inspired to compress the container one or more additional times. The additional compression pushes air down the stem, which can force the surgical prep solution out of the pad, resulting in undesirable dripping. In addition to dripping, the air may also cause the surgical prep solution to foam.

As used in connection with the present invention, the collapsible containers provide an original volume when filled with surgical prep solution and before dispensing of the surgical prep solution. After dispensing of the surgical prep solution, the compressed containers can be described as having a collapsed volume less than the original volume. The collapsible containers of the present invention preferably recover about 50% or less (more preferably about 25% or less) of the difference between the original volume and the collapsed volume within 30 seconds of dispensing a majority of the surgical prep solution in the container.

It may be further preferred that the container be impermeable to ethylene oxide gas, which allows the container to be sterilized by conventional ethylene oxide sterilizers without allowing ethylene oxide to penetrate the container. Penetration of ethylene oxide into the container has the potential to create toxic products within the surgical prep solution. This may be especially true with surgical prep solutions including iodine, in which 2-iodoethanol (iodohydrin) can be formed with exposure to ethylene oxide.

Preferred impermeable containers do not allow more than 100 ppm ethylene oxide into the container during exposure to ethylene oxide gas during sterilization, preferably less than 50 ppm, more preferably less than 25, and most preferably less than 10 ppm. Ideally, the container is manufactured of materials that provide a complete barrier to ethylene oxide gas penetration (less than 1 ppm, which is the current detection limit).

Suitable containers for use in the present invention may preferably retain surgical prep solution even when aged at 50° C. for 28 days with no more than, e.g., a 2 percent net weight loss. This can be especially difficult with hydroalcoholic surgical prep solutions. One potentially suitable material for the containers may be, e.g., polymer/aluminum foil laminates.

The container also includes a spout through which the surgical prep solution is delivered from the container to the spreader element. Although spouts in the form of threaded male members are disclosed in connection with the illustrative embodiments, it should be understood that spouts used in connection with the containers may alternatively take any suitable form that can cooperate with the spreader element to deliver surgical prep solution from the container to the pad.

The spout may preferably include a container seal formed over its opening. More preferably, the container includes a sealed spout that is impermeable to ethylene oxide, e.g., a polyolefin/foil laminate seal. The seal may preferably be opened as the container is engaged with the spreader element.

In preferred embodiments of the present invention, the system is unvented when the container is properly connected to the spreading element. As used herein, unvented means that the only opening into the fluid path is through the orifice in the spreader element body. With an unvented system, compression of the container causes the surgical prep solution to rapidly travel through the passage and into the pad. This can be faster and more convenient than waiting for gravity to move the surgical prep solution into the pad as in prior art vented applicators. Preferred unvented systems require compression of the container to dispense the surgical prep solution in sufficient amounts to wet the pad.

It may also be preferred that at least the exterior surfaces of the spreader element and the container be sterile such that the applicator system can be used in an aseptic manner to apply the surgical prep solution. This may necessarily require that the spreader element and container be provided in a sterile package.

In some instances, it may be preferred that the spreader element include a receptacle at the proximal end of the stem.

In one aspect, the present invention provides an applicator system for surgical prep solution, the system including a spreader element and a collapsible container of surgical prep solution. The spreader element includes a body with an orifice; a pad attached to the body over the orifice; a stem comprising a distal end attached to the body and a passage extending between the distal end of the stem and a proximal end of the stem, wherein the passage is in fluid communication with the orifice at the distal end of the stem. The collapsible container includes surgical prep solution and a spout adapted to attach to the proximal end of the stem, wherein the surgical prep solution can be delivered to the passage for delivery to the pad. The collapsible container has an original volume and a collapsed volume after dispensing of the surgical prep solution. The collapsible container spontaneously recovers about 50% or less of the difference between the original volume and the collapsed volume within 30 seconds of dispensing of a majority of the surgical prep solution.

In another aspect, the present invention provides method of applying surgical prep solution by providing a spreader element including a body having an orifice; a pad attached to the body over the orifice; a stem having a distal end attached to the body and a passage extending between the distal end of the stem and a proximal end of the stem, wherein the passage is in fluid communication with the orifice at the distal end of the stem. The method further includes providing surgical prep solution in a collapsible container; attaching the collapsible container to the proximal end of the stem, wherein the surgical prep solution is in fluid communication with the passage of the stem; and dispensing the surgical prep solution into the passage by compressing the collapsible container, wherein the collapsible container has an original volume and a collapsed volume after dispensing of the surgical prep solution, and further wherein the collapsible container recovers about 50% or less of the difference between the original volume and the collapsed volume within 30 seconds of dispensing a majority of the surgical prep solution.

In another aspect, the present invention provides a method of manufacturing an applicator system for surgical prep solution, the method including providing a spreader element that includes a body having an orifice; a pad attached to the body over the orifice; and a stem comprising a distal end attached to the body and a passage extending between the distal end of the stem and a proximal end of the stem, wherein the passage is in fluid communication with the orifice at the distal end of the stem. The method further includes providing a collapsible container including surgical prep solution and a spout adapted to attach to the stem of the spreader element, wherein the surgical prep solution can be delivered to the passage for delivery to the pad. The collapsible container has an original volume and a collapsed volume after dispensing of the surgical prep solution, and the collapsible container recovers about 50% or less of a difference between the original volume and the collapsed volume within 30 seconds of dispensing of a majority of the surgical prep solution.

In another aspect, the present invention provides an applicator system for surgical prep solution. The system includes a spreader element and a collapsible container attached to the spreader element. The spreader element includes a body with an orifice and a pad attached to the body over the orifice. The spreader element also includes a stem with a distal end attached to the body and a passage extending between the distal end of the stem and a proximal end of the stem, wherein the passage is in fluid communication with the orifice at the distal end of the stem. The collapsible container retains surgical prep solution therein (until dispensed) and has an original volume and a collapsed volume after dispensing of the surgical prep solution, and further wherein the collapsible container recovers about 50% or less of a difference between the original volume and the collapsed volume within 30 seconds of dispensing a majority of the surgical prep solution. The container may also include a container seal retaining the surgical prep solution within the collapsible container.

In another aspect, the present invention provides an applicator system for surgical prep solution, the system including a container retaining surgical prep solution therein and a spreader element. The spreader element includes a body having an orifice and a pad attached to the body over the orifice. The spreader element also includes a stem with a distal end attached to the body and a passage extending between the distal end of the stem and a proximal end of the stem, wherein the passage is in fluid communication with the orifice at the distal end of the stem. Further, the spreader element includes a receptacle at the proximal end of the stem, the receptacle extending around at least a portion of a circumference of the container when the container is attached to the spreader element.

These and other features and advantages of the present invention are described below in connection with various illustrative embodiments of the invention.

DETAILED DESCRIPTION OF ILLUSTRATIVE EMBODIMENTS OF THE INVENTION

Figure 1:
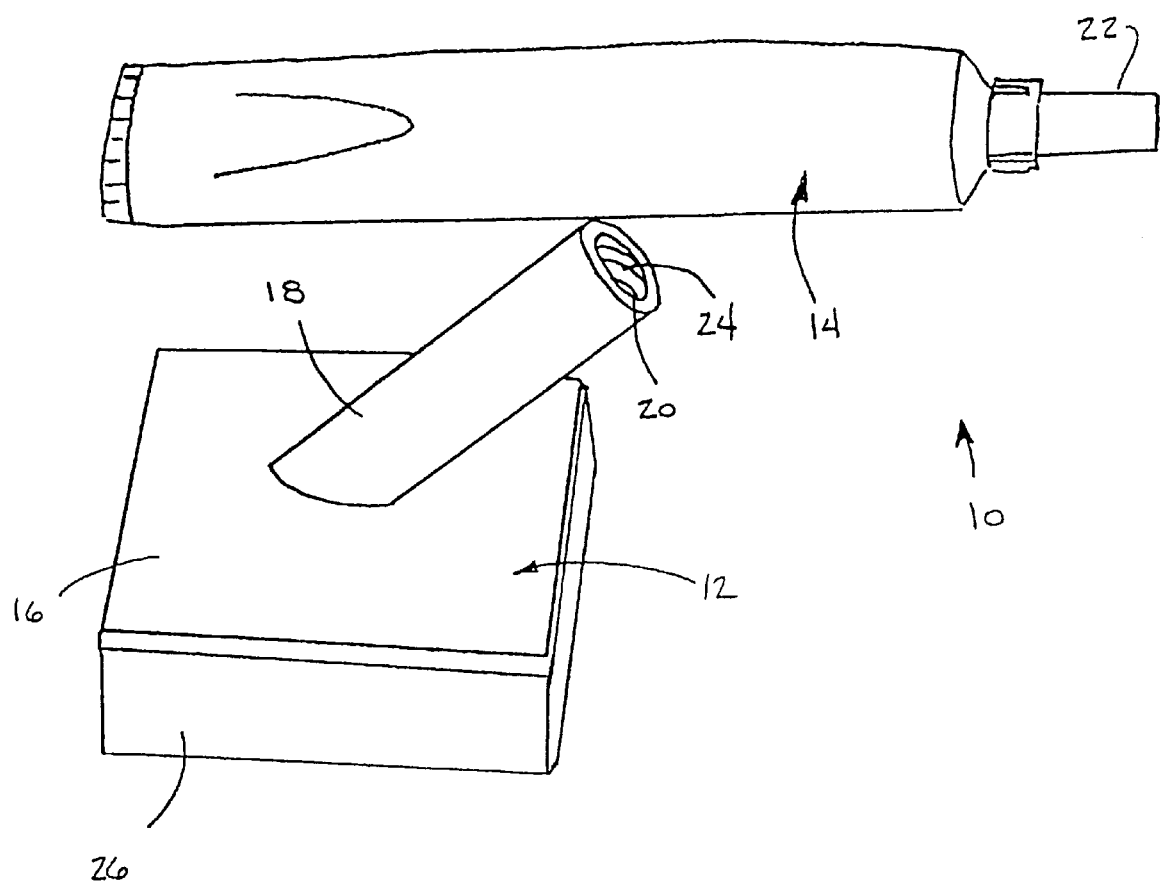
FIG. 1 is a perspective view of the elements of the applicator according to the present invention.
Figure 2:
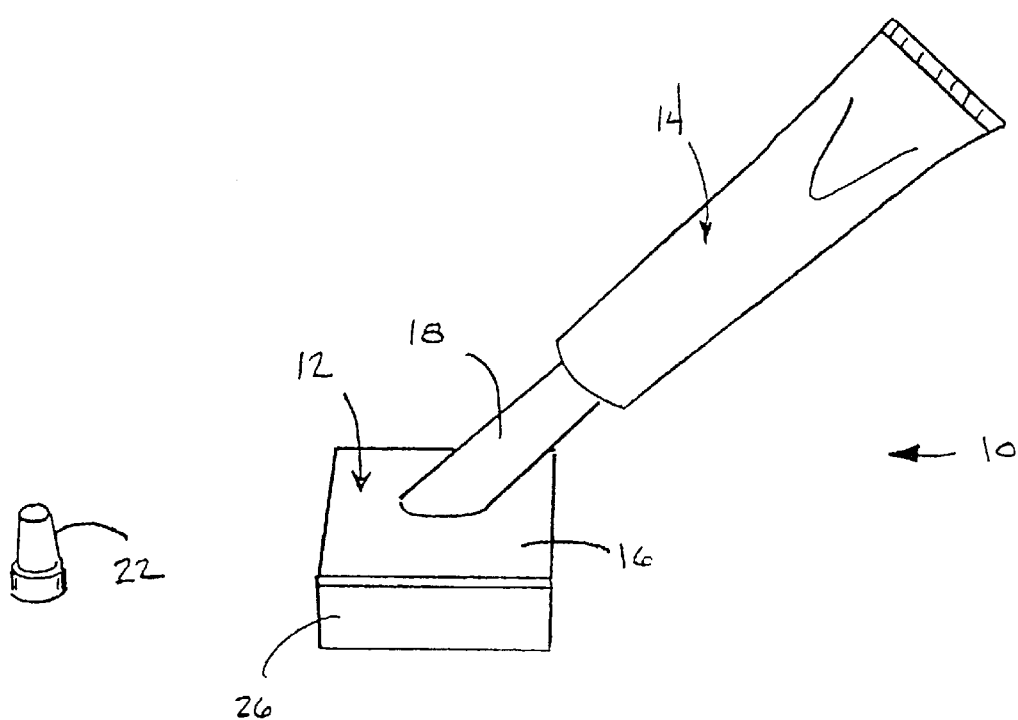
FIG. 2 is a perspective view of the elements of FIG. 1 in an assembled condition.
Figure 3:
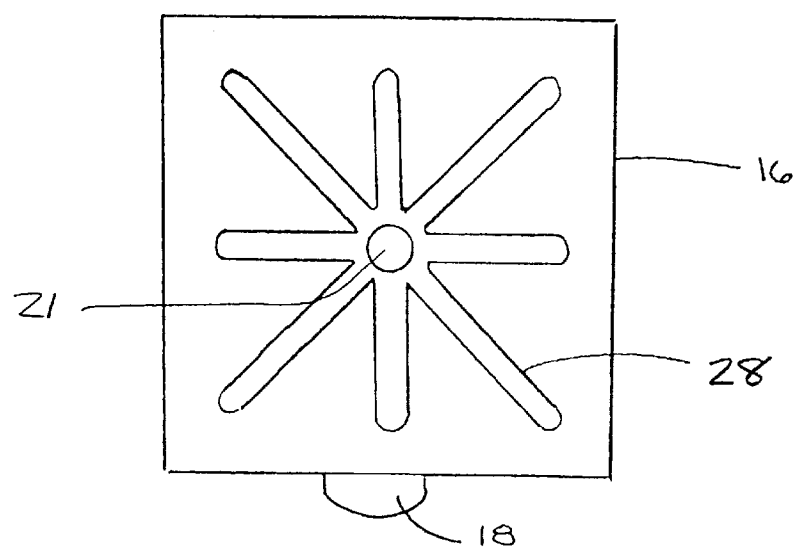
FIG. 3 is a detailed bottom view of the body of the spreader element with the foam pad removed.

Referring now to FIGS. 1–3, an illustrative embodiment of one applicator system according to the present invention is depicted. The applicator system 10 includes a spreader element 12 and a container 14. The container 14 is not attached to the spreader element 12 and is filled with surgical prep solution used to, e.g., prepare a patient for various medical or surgical procedures.

The spreader element 12 includes a body 16 and a stem 18. The stem 18 includes a passage 20 formed therethrough, the passage 20 being in fluid communication with an orifice 21 formed in the body 16.

The container 14 is depicted in FIG. 1 with an optional cap 22 covering an optional spout on the container 14. Connection of the container 14 to the spreader element 12 involves removing the cap 22 (if provided with the container 14) and attaching the spout of the container 14 to the proximal end of the stem 18 as depicted in FIG. 2.

The spout on the container 14 may preferably include threads that engage threads 24 formed in the passage 20 at the proximal end of the stem 18. It will be readily apparent that there are a number of alternative mechanical expedients used to connect the spout of the container 14 to the spreader element 12 such that the surgical prep solution does not leak at the junction between the container 14 and the spreader element 12, e.g., bayonet fittings, snap fittings, tapered press fittings, etc.

Referring to FIG. 2, a perspective view of the elements of FIG. 1 in an assembled condition is illustrated. The cap 22 has been removed, and the container 14 has been fitted onto the stem 18 so that the surgical prep solution in the container 14 can pass through the passage 20 to wet the pad 26.

It should be noted that although the spreader element 12 and container 14 may be provided disassembled as illustrated in FIG. 1, it may be preferred to provide the two components as assembled in FIG. 2. If so provided, it may also be preferred that the container 14 be sealed such that any surgical prep solution is retained within the container 14 such that the surgical prep solution is prevented from reaching the pad 26. The spreader element 12 and container 14 may be connected by a threaded connection (see, e.g., FIGS. 7 & 8 below) in which a portion of the complementary threads are engaged to retain the two components in an assembled state. When so provided, additional rotation of the container 14 relative to the spreader element 12 may open a seal to allow delivery of the surgical prep solution to the pad 26.

In another potential alternative, the container 14 may be provided with a bayonet connection, snap-lock connection, etc. to the spreader element 12 such that rotation and/or translational movement of the container 14 along the longitudinal axis of the stem 18 cause the container 14 to open, thereby allowing the surgical prep solution to move into the pad 26. Other connections that achieve the desired result of retaining the components in an assembled state while preventing delivery of the surgical prep solution to the pad 26 can also be used.

The stem 18 may preferably be elongated such that the handle is at least 2.5 cm, more preferably at least 5 cm, and most preferably at least 6 cm from the top of the body 16 of the spreader element 12. In this manner, a clinician applying the surgical prep solution can do so with a reduced risk of contaminating his gloved hands by contact with the patient. In other applications, an elongated stem may advantageously provide access to body orifices, e.g., the vagina.

The spreader element 12 also includes a pad 26 attached to the body 16 such that the pad 26 covers the orifice 21 of the body 16. The pad 26 may be formed of any suitable material or materials that will absorb the surgical prep solution and allow it to be delivered to the patient's skin. Exemplary pads may be manufactured of materials that include, but are not limited to, open cell foams (e.g., open cell polyurethane foams), fibrous materials (woven or nonwoven), etc.

Surgical prep solutions used in connection with the present invention may have very low viscosities, e.g., 100 cps or less, possibly 50 cps or less, and even 20 cps or less (measured at 23° C.). Furthermore, many preferred surgical prep solutions contain either alcohol (e.g., 2 propanol, n-propanol, or ethanol) or surfactants. As a result, the surface tension of the surgical prep solutions used in connection with the present invention may be relatively low, e.g., 50 dyne/cm or less, possibly 40 dyne/cm or less, and even 30 dyne/cm or less.

This combination of low viscosity and low surface tension can make filling the pad 26 without dripping a difficult challenge. For this reason, in preferred embodiments the spreader element 12 preferably includes a flow restrictor. In one embodiment, the flow restrictor may be provided in the form of the entire passage 20 may be of a relatively small cross-sectional area. For example, in one preferred embodiment used with a hydroalcoholic surgical prep solution, a circular cylindrical passage 20 having a diameter of about 2 mm and a length of about 55 mm may provide a suitable flow restrictor.

In another manner of characterizing a flow restrictor in terms of the dimensions of passage 20, it may be preferred that the passage have a ratio of length of the passage between the distal and proximal ends of the stem to a minimum cross-sectional dimension of the passage of about 20:1 or more. This definition would include passages with uniform cross-sectional areas along their length or those in which only a portion of the passage has a reduced cross-sectional area.

Alternatively, the flow restrictor may be provided by an orifice 21 that is small enough to restrict flow from the passage 20. In another alternative, the flow restrictor may be provided in the spout of the container 14, such that only a limited flow of surgical prep solution from the container 14 is provided as the container 14 is compressed.

Referring now to FIG. 3, a detailed bottom view of the body 16 of the spreader element 12 with the pad 26 removed is depicted. The body 16 includes distribution channels 28 in fluid communication with the orifice 21. In the depicted embodiment, the distribution channels 28 radiate outward from the orifice 21, although this is not a requirement of the invention. It may be preferred to provide only a single orifice 21 in the body 16. Alternatively, more than one orifice may be provided in the body 16.

The pad 26 may preferably be sealed around the outer periphery of the body 16 of the spreader element 12. The pad seal formed between the pad 26 and the body 16 is preferably leak-proof to force the surgical prep solution to travel through the pad 26 rather than pass between the pad 26 and the body 16, where it is more likely to drip from the spreader element 12. Suitable pad seals may include, e.g., but are not limited to, hot melt, pressure sensitive, and curable adhesives; RF weldable gaskets, ultrasonic welding, thermal welding, etc.

Figure 4:
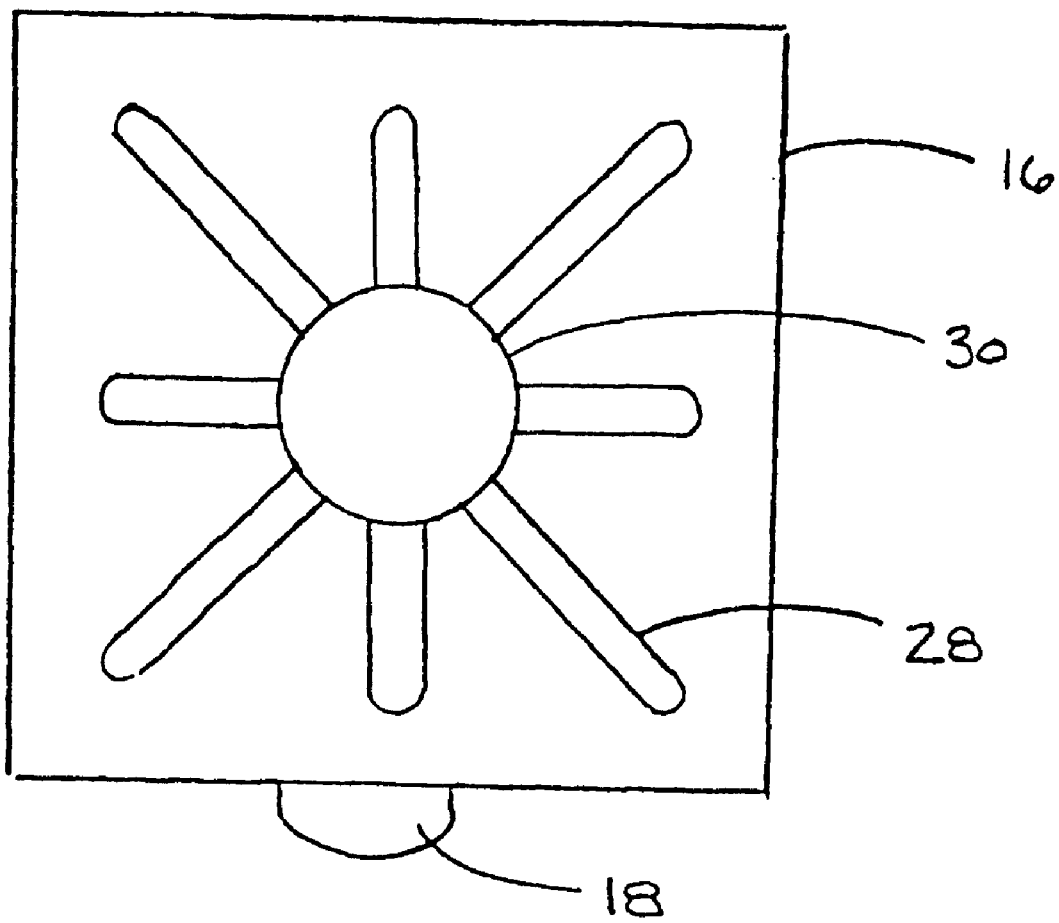
FIG. 4 is a bottom view of an alternate embodiment of the body of the spreader element with the foam pad removed.

Referring now to FIG. 4, a detailed bottom view of an alternate embodiment of the body 16 of the spreader element 12, with the foam pad 26 removed, is illustrated. The view is similar to that of FIG. 3, but in this embodiment a liquid impermeable adhesive coated film patch 30 has been adhered to the underside of the body 16 so that the surgical prep solution must travel along at least some of at least one of the distribution channels 28 before it can begin to soak into the pad 26. Alternatively, the film patch 30 can be placed on or adhere to the pad directly in front of passage 20 of FIG. 3. With a 5×5 cm open-celled polyurethane pad, a 1.75 cm diameter patch has proven useful. This patch is thus about 35 percent of the width of the pad. Patches that are 25–50 percent of the pad width may be considered suitable.

Figure 5:
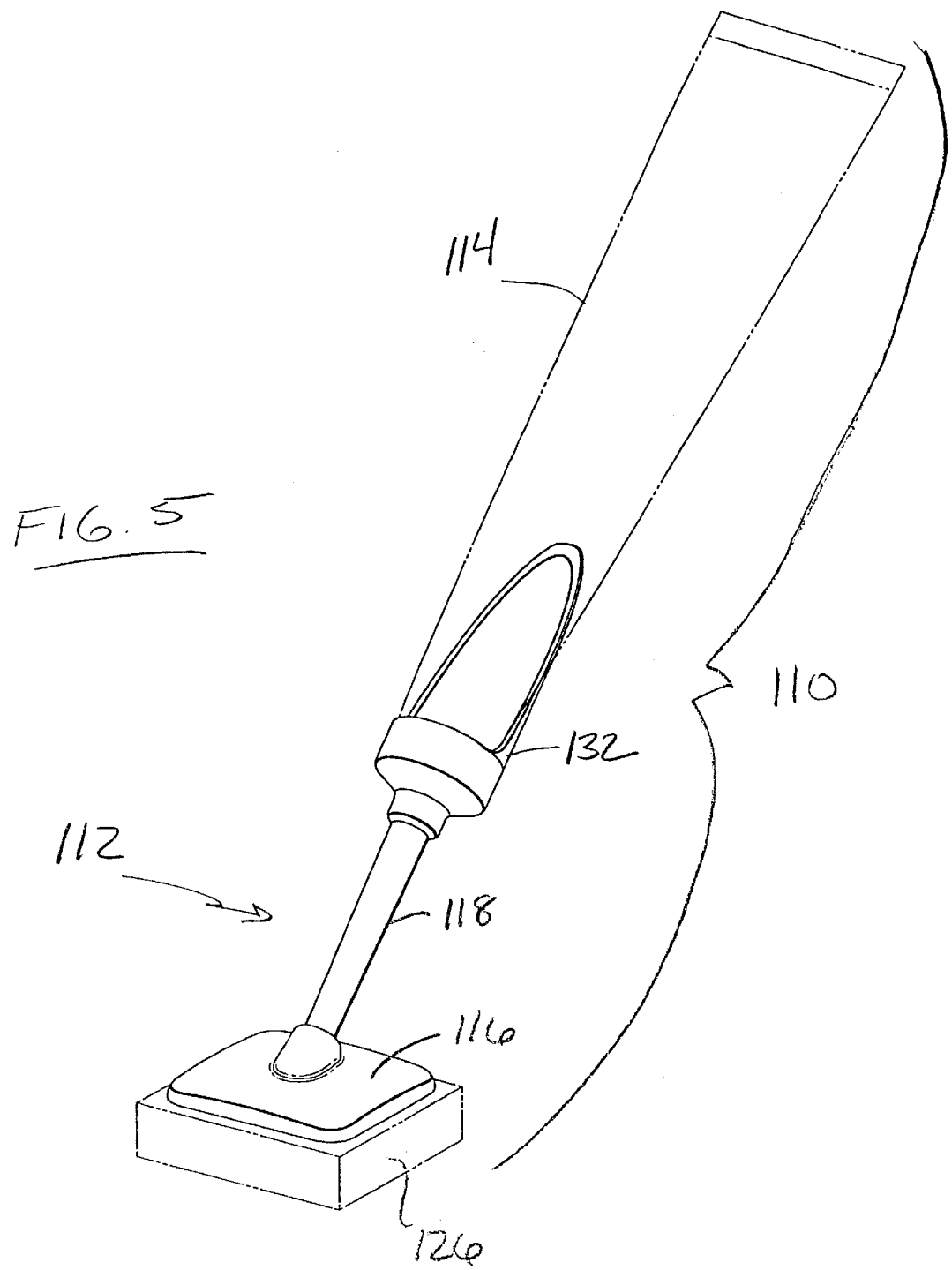
FIG. 5 is a perspective view of an alternate embodiment of an applicator system, with the container depicted in broken lines to expose all of the spreader element.

Referring now to FIG. 5, a perspective view of an alternate embodiment of the applicator system 110 is illustrated. The applicator system 110 includes a spreader element 112 and a container 114 that holds a surgical prep solution. The spreader element 112 includes a body 116 and a stem 118.

In the depicted embodiment, the stem 118 includes a receptacle 132 at its proximal end that is shaped to receive the container 114. Conveniently, the receptacle 132 may form, e.g., a flange that assists in aligning the container 114 with the stem 118 for convenient attachment. For example, when the spout of the container 114 and the stem 118 include complementary threads, the receptacle 132 may assist the user in properly aligning the threads on the opposing elements. In addition, the receptacle 132 may impart additional rigidity that facilitates application of the surgical prep solution.

The receptacle 132 may preferably extend around at least a portion of the circumference of the container 114 for a portion of the length of the container 114 past any spout used to connect the container to the spreader element 112 (up to and including completely encircling the container 114). It may, however, be preferred that the receptacle 132 extend about only a portion of the circumference of the container 114 in a manner as illustrated in FIG. 5. Limiting circumferential coverage of the container 114 by the receptacle 132 may be advantageous by, for example, providing the user with a better view while making the connection between the container 114 and the spreader element 112. Another reason to limit the circumferential coverage of the receptacle 132 is to allow the user to prompt an additional flow of the surgical prep solution from the container 114 into the pad 126 with a slight application of thumb pressure to the exposed surface of the container 114 opposite the receptacle 132.

Figure 6:
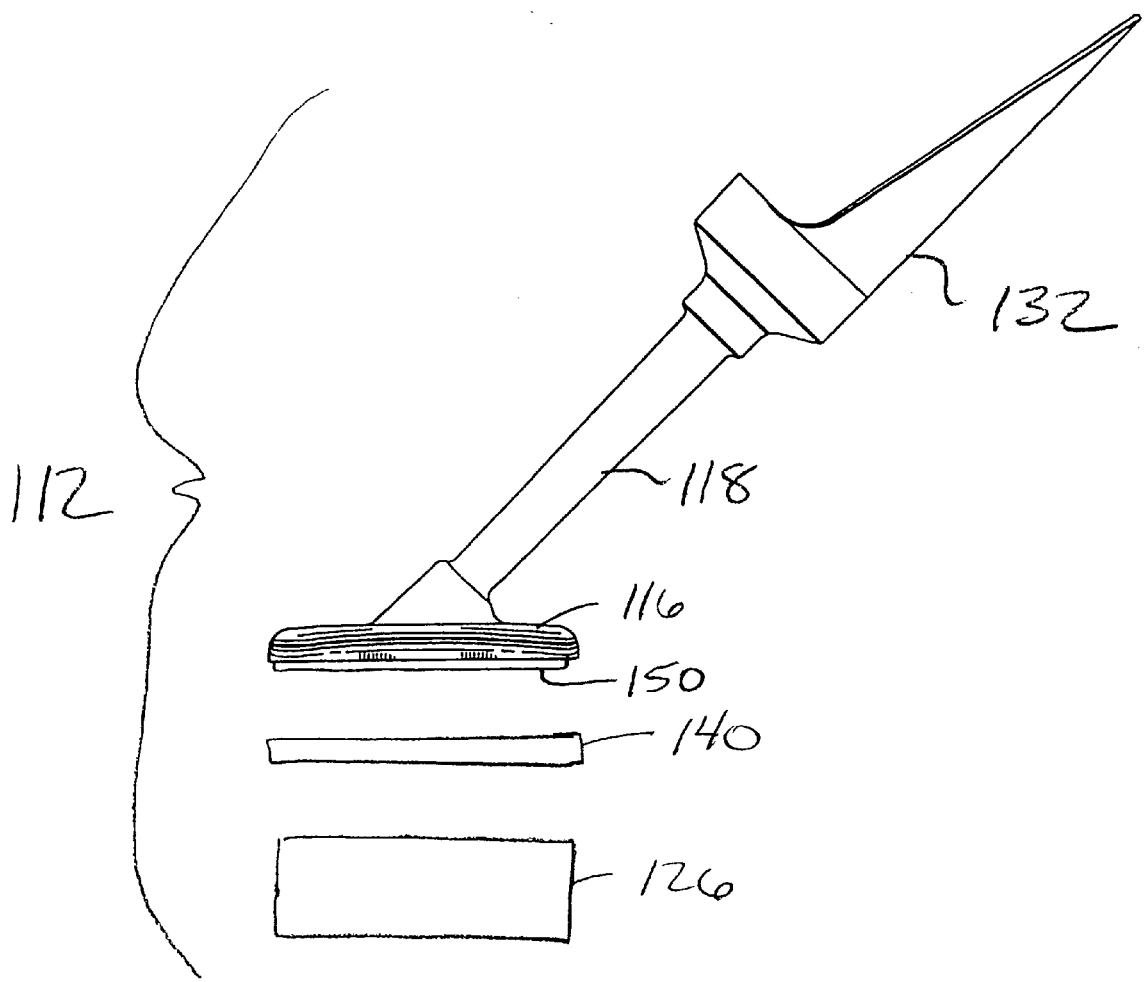
FIG. 6 is an exploded view of an alternative spreader element.

Referring now to FIG. 6, an exploded view of the spreader element 112 is depicted and includes an optional metering layer 140 between the pad 126 and the body 116. The optional metering layer 140 may provide an additional flow restrictor or an alternative flow restrictor between the pad 126 and container 114 to restrict flow of the surgical prep solution.

One potential metering layer 140 may be provided in the form of a porous film that includes a pattern of frusto-conical openings formed therethrough, such that the openings are smaller on one side of the film and larger on the opposite side of the film. Suitable orientation of the metering layer may provide the desired amount of flow restriction. One potential product having this structure replicated in a polyethylene film is available from Tredegar Corporation (Richmond, Va.) under the tradename VISIPORE (Product No. S-6010025).

Also depicted in FIG. 6 is a seal ridge 150 used in forming a pad seal in the form of weld between the body 116 and the pad 126 in one embodiment of the present invention. The seal ridge 150 extends about the periphery of the body 116 and is preferably continuous such that a continuous pad seal can be formed. The seal ridge 150 may preferably be formed of a thermoplastic material. In some embodiments, substantially the entire spreader element 112 may be manufactured of a thermoplastic material. Preferably, the pad seal can be formed through the metering fabric 140 (if the metering fabric 140 is present).

Regardless, by providing at least the seal ridge 150 of a thermoplastic material, the seal ridge 150 may be at least partially melted, followed by application of the pad 126 to the softened seal ridge 150 under pressure until the seal ridge 150 cools. The result is a fluid tight pad seal in the form of a weld between the body 116 and the pad 126. The seal ridge 150 may, for example, be heated by conduction from a release-coated heated platen, hot air, etc.

Figure 7:
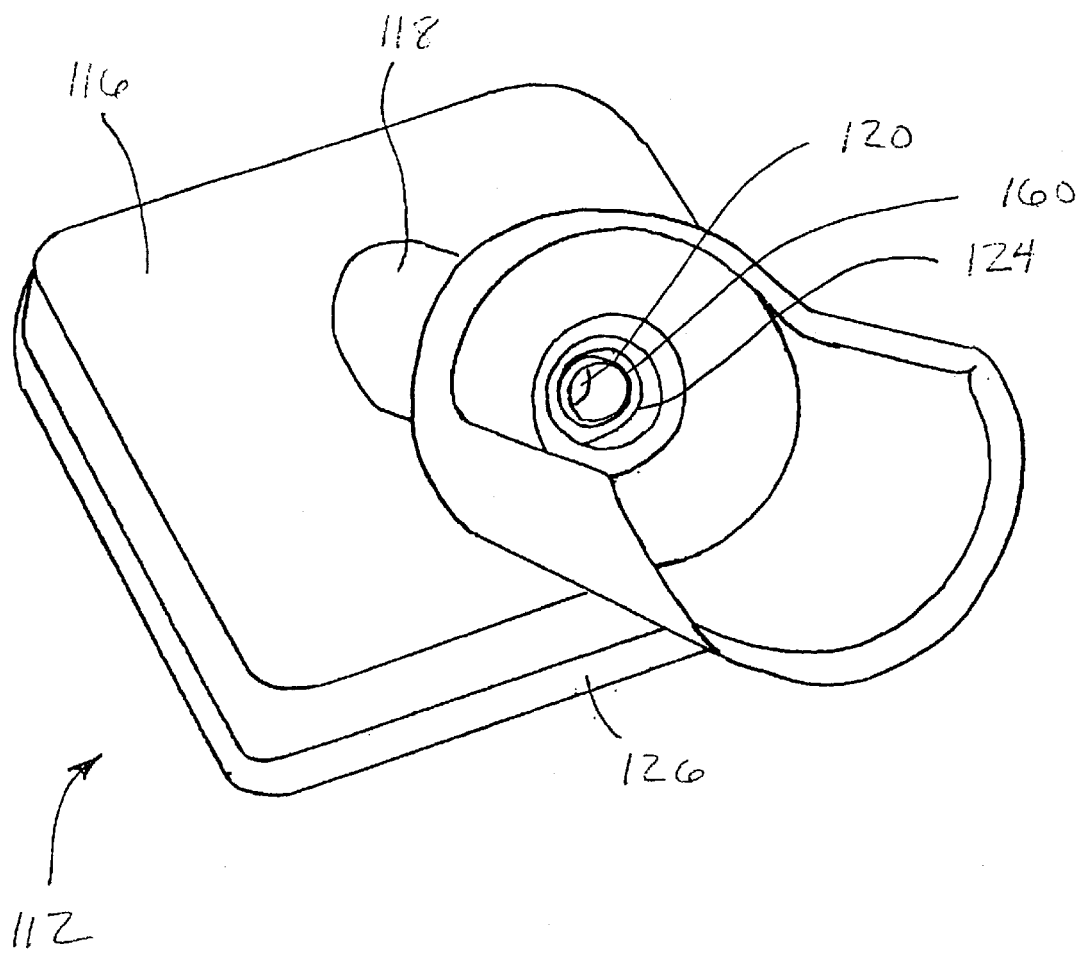
FIG. 7 is a perspective view of the spreader element of the applicator of FIGS. 5 and 6 in which the container is removed to illustrate the proximal end of the stem.

Referring now to FIG. 7, a perspective view of the spreader element 112 of is depicted with the container removed to expose the proximal end of the stem 118. In this view the passage 120 for conducting the surgical prep solution from the container through the stem 118 and into the pad 126 can be seen.

Figure 8:
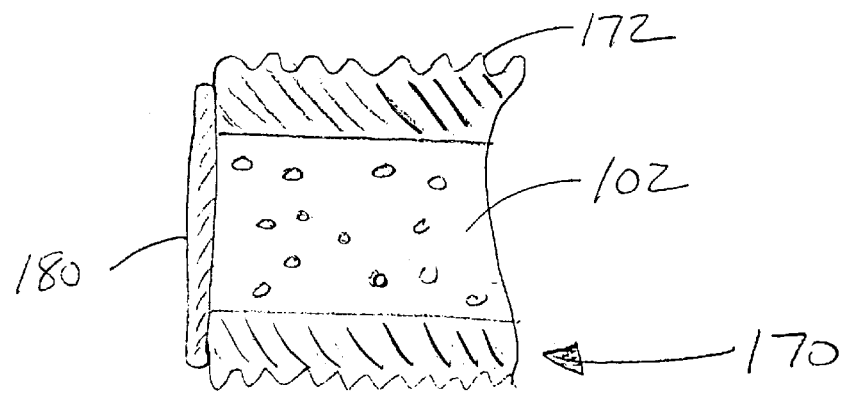
FIG. 8 is a cross-sectional view of a spout with container seal for use on a container of the present invention.

FIG. 8 illustrates one spout 170 that may be used on a container in connection with the present invention. The spout 170 also includes an optional container seal 180 to prevent leakage of the surgical prep solution 102 from the spout 170 (and associated container) before connection to the spreader element. The container seal 180 may be, e.g., an adhesive or heat bonded foil laminate seal or other suitable construction that prevents unwanted leakage of the surgical prep solution 102. It may be preferred that the seal 180 also provide an effective barrier to the penetration of ethylene oxide gas during sterilization.

Threads 124 may preferably be provided in the proximal end of the stem 118 for attaching the spout 170 to the spreader element 112. The threads 124 preferably engage complementary threads 172 on the spout 170. Other attachment techniques and structures may be used in place of threads as noted above.

Turning back to FIG. 7, a piercing element 160 in the form of an annular die is provided in the passage 120 of spreader element 112. The piercing element 160 may be provided to, e.g., open a seal on the container such as the container seal 180, thereby allowing the surgical prep solution 102 to move into the passage 120 and to the pad 126. Preferred annular dies may include one or more protrusions or notches on the cutting edge of the die to initiate tearing of any seal. The depicted piercing element 160 is in the form of an annular die located within the passage 120. As a result, as the spout 170 is threaded onto the stem 118, the piercing element 160 opens the container seal 180.

It may be preferred that the various components are sized and shaped so that the threads are almost fully engaged prior to opening of the container seal 180. This may reduce or eliminate leakage at the junction between the spout 170 and the stem 118 even if the container is not held upright during assembly. While the illustrated embodiment is shown with an annular die as a piercing element 160, other arrangements which pierce the seal may be used such as a projection, which may be centered or off-center within the passage 120.

Further, the piercing element (in whatever form) may be formed as an integral part of the stem 118, or it may be provided as a separate insert assembled into the stem after the stem 118 is manufactured.

Figure 9:
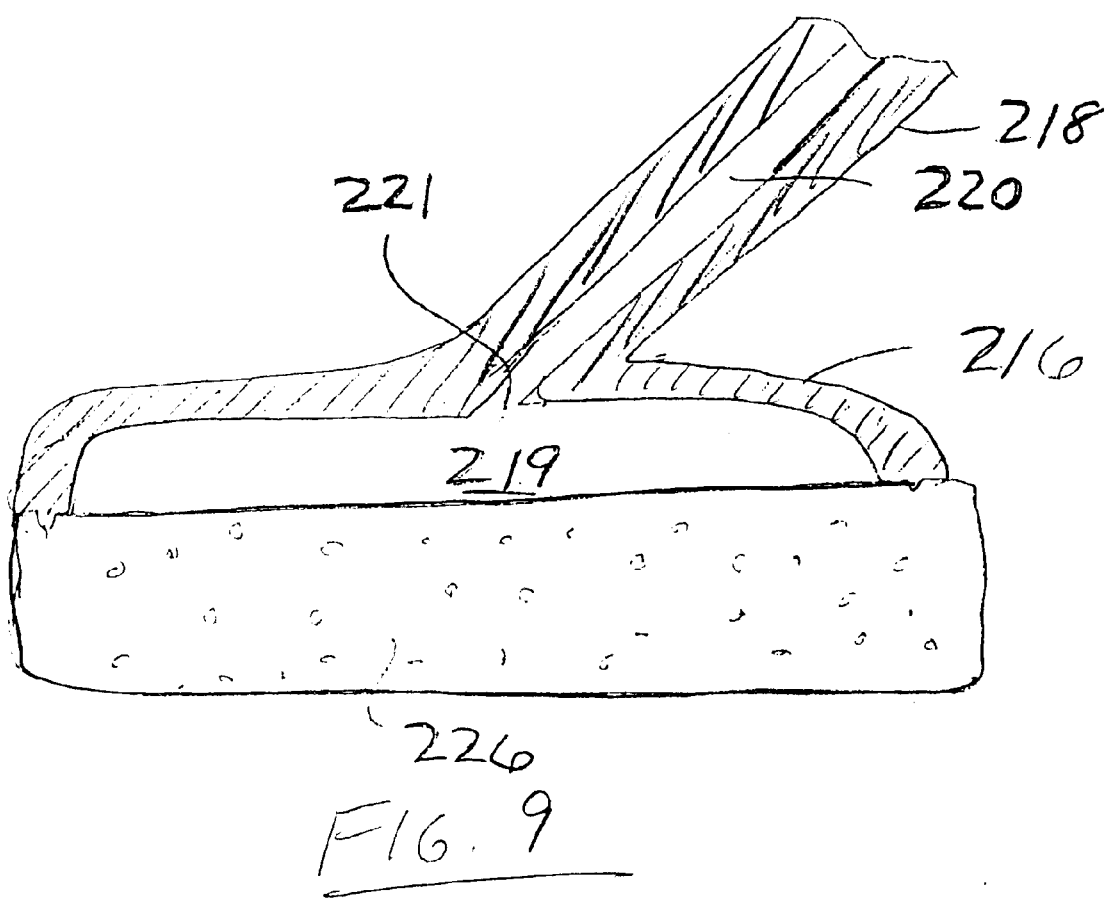
FIG. 9 is a cross-sectional view of a portion of another spreader element of the invention.

FIG. 9 depicts an additional optional feature of the present invention in the form of a plenum 219 formed between the pad 226 and the body 216. The plenum 219 receives surgical prep solution traveling along the passage 220 in stem 218 through the orifice 221 (over which the pad 226 is attached). The plenum 219 may help to evenly distribute the surgical prep solution to the pad 226.

EXAMPLES

Advantages of the invention are illustrated by the following examples. However, the particular materials and amounts thereof recited in these examples, as well as other conditions and details, are to be interpreted to apply broadly in the art and should not be construed to unduly limit the invention.

Example 1

A body generally as depicted in the drawing was machined from two pieces of Delrin plastic such that the stem extended away from the rest of the body at an angle of about 45 degrees. The main plane of the body was approximately 5 cm by 5 cm, and the stem was about 4.8 cm in length. The stem was threaded to accept complementary threads on the container element. Distribution channels were machined into the bottom surface of the body by end milling 0.29 cm diameter grooves in the body in such a way as to create a eight individual paths from the center of the body nearly to its edge. The artisan will perceive that injection molding will be a preferred method of fabricating the body in quantity, and that other polymers, such as polyolefins, will be suited to such manufacturing.

A foam pad, commercially available from Illbruck, Minneapolis, Minn. and identified as P 90 Z Beige Clickable foam pad was adhesively attached to the body using a hot melt adhesive. A bead of hot melt adhesive was applied to the perimeter of the foam pad and the pad and Delrin plastic connector were brought into contact with one another for about 30 seconds.

A polymer/foil/polymer three-layer tube, where the foil is aluminum and the polymer is polyethylene, available from Expac Corporation, Montvale, N.J. was used as the container element to contain 26 ml of DURAPREP surgical prep solution (including isopropanol/water, acrylate terpolymer, iodine and sodium iodine, commercially available from 3M Company). The tube included threads on the spout complementary to those provided on the stem. The tube was heat sealed using conventional methods.

The sealed tube of surgical prep solution was opened by removing the cap, and for the case where an induction sealed foil covers the opening, the foil seal was perforated, and the tube of surgical prep solution was attached to the spreader element connector by the threading the spout into the threads in the stem. The container element was gripped in the manner of a handle, and the applicator was used to spread the surgical prep solution onto the torso of a patient. A smooth, even application was achieved without dripping.

Example 2

About 21 g of DURAPREP Surgical Solution (a hydroalcoholic solution containing 74% w/w isopropyl alcohol and 0.7% available iodine) was filled into 1 oz. Expac poly film/foil/polyfilm laminate tubes available from Expac Corp. of Hopkins, Minn., as model number 5485X. The exact weight of the tube before and after filling was recorded to 4 decimal places. The tubes were heat sealed. Two sets of 10 tubes were prepared. Set A had a foil seal welded over the tip. Set B did not. Both sets of tubes had a polycap screwed on tightly over the tip. The tubes were placed in a recirculated oven at 50° C. for 28 days. The tubes were removed periodically and weighed. The weight was recorded to four decimal places. The following results were obtained:

| | % Weight Loss After Aging At 50° C. | |
|---|---|---|
| Day | Set A Mean | Set B Mean |
| 0 | 0 | 0 |
| 3 | 0.0332 | 0.0419 |
| 7 | 0.0408 | 0.0577 |
| 10 | 0.0503 | 0.0651 |
| 14 | 0.0534 | 0.0782 |
| 17 | 0.0571 | 0.0838 |
| 21 | 0.0689 | 0.0906 |
| 24 | 0.0761 | 0.1058 |
| 28 | 0.09 | 0.1155 |

The data indicates that even after 28 days at 50° C. the mean value of the Set A samples with the foil seal was only 0.0900% while the set without the seal was only 0.1155%. This proves that this poly/foil construction is an exceptional barrier to water and alcohol even under exaggerated conditions.

Example 3

The same tube construction used in Ex. 2 was filled with 26 g water. Ten tubes were sealed and capped without the foil cap seal. The tubes were ETO sterilized in a 3M Sterivac Model 4 XL ethylene oxide sterilizer. The tubes were then aerated for one hour twenty minutes in a 3M model XL Aeratra cabinet. This results in an exposure to ethylene oxide gas for about four hours and ten minutes at 500 millibars and an aeration time of one hour and twenty minutes. The samples were sent to Biotest Labs in Minneapolis, Minn., for testing. The contents of the tubes by gas chromatography for residue of ethylene oxide, ethylene chlorohydrin and ethylene glycol. The presence of these compounds in the contents of the tubes would indicate that the tube allowed some of the ethylene oxide sterilant to enter the tube during the sterilization cycle.

Results

All of the containers were found to have non-detectable levels of ethylene chlorohydrin and ethylene glycol. Six of the ten Expac containers were evaluated to have non-detectable levels of ethylene oxide. Four of the ten Expac containers were evaluated to have 1 part-per-million (ppm) of ethylene oxide, corresponding to 0.021 mg of ethylene oxide per 26 ml of tap water. The detection limit of the gas chromatograph used to complete the analysis is 1 ppm.

The reference document under which the test was conducted was ANSI/AAMI/ISO 10993-7 BIOLOGICAL EVALUATION OF MEDICAL DEVICES- PART 7: ETHYLENE OXIDE STERILIZATION AND ANSI /AAMI ST30: DETERMINING RESIDUAL ETHYLENE CHLOROHYDRIN AND ETHYLENE GLYCOL IN MEDICAL DEVICES. The containers appear to provide an effective barrier to ethylene oxide sterilization.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

What is claimed is:

1. An applicator system for surgical prep solution, the system comprising:
    a spreader element comprising:
        a body comprising an orifice;
        a pad attached to the body over the orifice;
        a stem comprising a distal end attached to the body and a passage extending between the distal end of the stem and a proximal end of the stem, wherein the passage is in fluid communication with the orifice at the distal end of the stem;
    a collapsible container comprising:
    surgical prep solution;
    a spout adapted to attach to the proximal end of the stem, wherein the surgical prep solution can be delivered to the passage for delivery to the pad;
        wherein the collapsible container comprises an original volume and a collapsed volume after dispensing of the surgical prep solution, and further wherein the collapsible container recovers about 50% or less of a difference between the original volume and the collapsed volume within 30 seconds of dispensing a majority of the surgical prep solution.

2. The system of claim 1, wherein the collapsible container recovers about 25% or less of a difference between the original volume and the collapsed volume within 30 seconds of dispensing a majority of the surgical prep solution.

3. The system of claim 1, wherein the surgical prep solution comprises iodine or chlorhexidine.

4. The system of claim 3, wherein the collapsible container is substantially impermeable to ethylene oxide gas.

5. The system of claim 1, wherein the spreader element further comprises a pad seal between the pad and the body.

6. The system of claim 5, wherein the pad seal comprises a weld such that the pad is welded to the body.

7. The system of claim 6, wherein the spreader seal comprises a seal ridge formed on the body.

8. The system of claim 7, wherein the seal ridge extends continuously about the periphery of the body.

9. The system of claim 6, wherein the spreader seal comprises a seal ridge formed on the body, the seal ridge extending continuously about the periphery of the body, and further wherein the weld comprises the seal ridge.

10. The system of claim 1, wherein the spout comprises a container seal, and further wherein the spreader element comprises a piercing element adapted to open the container seal when the spout is attached to the stem.

11. The system of claim 7, wherein the piercing element comprises an annular die.

12. The system of claim 11, wherein the annular die comprises one or more protrusions or notches adapted to initiate tearing of the container seal.

13. The system of claim 1, further comprising a flow restrictor.

14. The system of claim 13, wherein the flow restrictor comprises the passage, and further wherein the passage comprises a ratio of length of the passage between the distal and proximal ends to a minimum cross-sectional dimension of the passage of about 20:1 or more.

15. The system of claim 13, wherein the flow restrictor comprises the orifice.

16. The system of claim 1, wherein the spreader element and the container comprise sterile exterior surfaces.

17. A method of applying surgical prep solution, the method comprising:
providing a spreader element comprising a body comprising an orifice; a pad attached to the body over the orifice, a stem comprising a distal end attached to the body and a passage extending between the distal end of the stem and a proximal end of the stem, wherein the passage is in fluid communication with the orifice at the distal end of the stem;
providing surgical prep solution in a collapsible container;
attaching the collapsible container to the proximal end of the stem, wherein the surgical prep solution is in fluid communication with the passage of the stem; and
dispensing the surgical prep solution into the passage by compressing the collapsible container, wherein the collapsible container comprises an original volume and a collapsed volume after dispensing of the surgical prep solution, and further wherein the collapsible container recovers about 50% or less of a difference between the original volume and the collapsed volume within 30 seconds of dispensing a majority of the surgical prep solution.

18. The method of claim 17, wherein the collapsible container comprises a container seal and the spreader element comprises a piercing element, and further wherein attaching the collapsible container to the proximal end of the stem comprises piercing the container seal with the piercing element.

19. The method of claim 18, wherein the piercing element comprises an annular die comprising one or more protrusions or notches to initiate tearing of the container seal.

20. The method of claim 17, wherein the container comprises a container seal and the spreader element comprises a piercing element, and further wherein attaching the container to the stem comprises piercing the container seal with the piercing element.

21. The method of claim 17, wherein the surgical prep solution comprises iodine or chlorhexidine, and further wherein the collapsible container is substantially impermeable to ethylene oxide gas before the dispensing.

22. The method of claim 17, wherein the spreader element further comprises a pad seal between the pad and the body.

23. The method of claim 22, wherein providing the spreader element comprises welding the pad to the body to form the pad seal.

24. A method of manufacturing an applicator system for surgical prep solution, the method comprising:
providing a spreader element comprising a body comprising an orifice; a pad attached to the body over the orifice; a stem comprising a distal end attached to the body and a passage extending between the distal end of the stem and a proximal end of the stem, wherein the passage is in fluid communication with the orifice at the distal end of the stem;
providing a collapsible container comprising surgical prep solution and a spout adapted to attach to the stem of the spreader element, wherein the surgical prep solution can be delivered to the passage for delivery to the pad;
wherein the collapsible container comprises an original volume and a collapsed volume after dispensing of the surgical prep solution, and further wherein the collapsible container spontaneously recovers about 50% or less of a difference between the original volume and the collapsed volume within 30 seconds of dispensing a majority of the surgical prep solution.

25. The method of claim 24, wherein the surgical prep solution comprises iodine or chlorhexidine, and further wherein the collapsible container is substantially impermeable to ethylene oxide gas.

26. The method of claim 24, wherein the spreader element further comprises a pad seal between the pad and the body.

27. The method of claim 26, wherein providing the spreader element comprises welding the pad to the body to form the pad seal.

28. The method of claim 27, wherein the body comprises a seal ridge, and further wherein the welding comprises welding the seal ridge to the pad.

29. The method of claim 27, wherein the body comprises a seal ridge extending continuously about the periphery of the body, and further wherein the welding comprises welding the seal ridge to the pad.

30. An applicator system for surgical prep solution, the system comprising:
a spreader element comprising:
a body comprising an orifice;
a pad attached to the body over the orifice;
a stem comprising a distal end attached to the body and a passage extending between the distal end of the stem and a proximal end of the stem, wherein the passage is in fluid communication with the orifice at the distal end of the stem;
a collapsible container attached to the proximal end of the stem, the collapsible container retaining surgical prep solution therein;
wherein the collapsible container comprises an original volume and a collapsed volume after dispensing of the surgical prep solution, and further wherein the collapsible container recovers about 50% or less of a difference between the original volume and the collapsed volume within 30 seconds of dispensing a majority of the surgical prep solution.

31. The system of claim 30, wherein the container comprises a container seal retaining the surgical prep solution within the collapsible container.

32. An applicator system for surgical prep solution, the system comprising:
a collapsible container retaining surgical prep solution therein; and
a spreader element comprising:
a body comprising an orifice;
a pad attached to the body over the orifice;
a stem comprising a distal end attached to the body and a passage extending between the distal end of the stem and a proximal end of the stem, wherein the passage is in fluid communication with the orifice at the distal end of the stem; and
a receptacle at the proximal end of the stem, the receptacle extending around at least a portion of a circumference of the container when the container is attached to the spreader element;
wherein the collapsible container comprises an original volume and a collapsed volume after dispensing the surgical prep solution, and further wherein the collapsible container recovers about 50% or less of a difference between the original volume and the collapsed volume within 30 seconds of dispensing a majority of the surgical prep solution.

33. The system of claim 32, wherein the receptacle extends around only a portion of the circumference of the container when the container is attached to the spreader element.

* * * * *